(12) United States Patent
Hofman

(10) Patent No.: US 7,376,215 B2
(45) Date of Patent: May 20, 2008

(54) MEASUREMENT OF ASH COMPOSITION USING SCANNING HIGH VOLTAGE X-RAY SENSOR

(75) Inventor: Gertjan J. Hofman, North Vancouver (CA)

(73) Assignee: Honeywell International Inc., Morristown, NJ (US)

( * ) Notice: Subject to any disclaimer, the term of this patent is extended or adjusted under 35 U.S.C. 154(b) by 259 days.

(21) Appl. No.: 11/318,889

(22) Filed: Dec. 27, 2005

(65) Prior Publication Data
US 2007/0147584 A1    Jun. 28, 2007

(51) Int. Cl.
    *G01N 23/06* (2006.01)
(52) U.S. Cl. .......................... 378/53; 378/210
(58) Field of Classification Search .............. 378/51, 378/53, 98.9, 101, 111, 210
    See application file for complete search history.

(56) References Cited

U.S. PATENT DOCUMENTS

| | | | |
|---|---|---|---|
| 4,081,676 A | 3/1978 | Buchnea | |
| 4,815,116 A | 3/1989 | Cho | |
| 5,854,821 A | 12/1998 | Chase et al. | |
| 6,377,652 B1 | 4/2002 | Sturm | 378/53 |
| 6,421,415 B1 * | 7/2002 | Peczkis et al. | 378/46 |

FOREIGN PATENT DOCUMENTS

| | | |
|---|---|---|
| DE | 252889 A1 | 12/1987 |
| EP | 0394128 A2 | 10/1990 |
| WO | WO 00/71996 A2 | 11/2000 |

* cited by examiner

*Primary Examiner*—Jurie Yun
(74) *Attorney, Agent, or Firm*—Scully, Scott, Murphy & Presser PC

(57) ABSTRACT

A system, method and computer program product is provided that enables measurement and determination of the relative material composition of ash content in a paper product. While materials in ash content, e.g., $CaCO_3$, Clay, and $TiO_2$, have distinct x-ray absorption spectrum, by varying an X-ray gauge rapidly, measuring the absorption at each energy level and, comparing this to tables of fundamental physical parameters, the relative fractions of materials in ash content, e.g., $CaCO_3$, Clay, and $TiO_2$, can be extracted. The relative weights of other constituent materials found in web or sheet paper products are additionally determinable.

20 Claims, 4 Drawing Sheets

MEASUREMENT OF ASH COMPOSITION USING SCANNING HIGH VOLTAGE X-RAY SENSOR

FIELD OF THE INVENTION

The present invention relates to paper products generally, and specifically, to a novel technique for measuring composition of additives, e.g., ash, and particularly, the relative concentrations of ash material additives present in paper web or paper sheet material.

BACKGROUND OF THE INVENTION

Paper comprises cellulose and additives. One additive is referred to as 'ash' and is the remaining material when the paper is burned. Paper products generally contain "ash" to enhance printability, color and other physical aspects. The most common type of additive found in paper products include Clay, Calcium Carbonate ($CaCO_3$) and Titanium Dioxide ($TiO_2$) but there exist other types of additives. It is well known that the weight of the paper is referred to as the Basis Weight (BW); Dry Weight (DW) is the Basis Weight minus the weight of the remaining water in the paper; and, Percentage Ash is defined as the sum of the additives divided by the Dry Weight.

Most paper qualities depend on the amount of ash content so this is tightly controlled during paper production. During production, the total ash content of a paper product or sample must be determined. X-ray absorption or X-ray fluorescence techniques are typically used to measure the individual or total concentrations of these additives.

U.S. Pat. No. 5,854,821 describes an X-ray absorption measuring system and process for measuring the three common types of paper additives. To measure ash, the '821 patent utilizes two adjacently placed x-ray sources on one side of a paper web, and two corresponding adjacent detectors placed on the opposite side of the paper web with the first source operating at an energy level higher than the of the paper web with the first source operating at an energy level higher than the second source. It is asserted that improved composition detection for ash in paper can be achieved in this manner. However, one skilled in the art will notice that operating such a system is still subject to reduced accuracy since variance of each X-ray source must also be considered.

U.S. Pat. No. 6,377,652 also describes an X-ray absorption measuring system that utilizes a "measure and calibrate" approach whereby a single X-ray source using a multiple filter/detector arrangement is used to determine the total mineral content in sheet material having at least three mineral additive components. Measurement beams are directed through a continuously advancing paper web with each beam being received by a corresponding X-ray detector on the other side of the web. Signals representative of both the beam(s) and the detector(s) are received by a computer which then compares the signals and, using well-known or readily derived equations, computes the individual component concentrations of the mineral additives in the paper web.

Those skilled in the art will notice that the signals obtained in the three detectors by such an arrangement are only slightly different and thus result in very limited accuracy of the composition.

It would be highly desirable to provide a system for implementing a technique that enables detection of the relative material composition of ash content in paper material utilizing a simple scanning X-ray sensor gauge and known fundamental physics parameters concerning the ash contents.

SUMMARY OF THE INVENTION

A system, method and computer program product is provided that enables measurement and determination of the relative material composition of ash content in a paper product. While materials in ash content, e.g., $CaCO_3$, Clay, and $TiO_2$, have distinct x-ray absorption spectrum, by varying the X-ray gauge rapidly, and measuring the absorption at each energy level and comparing this to tables of fundamental physical parameters, the relative fractions of materials in ash content, e.g., $CaCO_3$, Clay, and $TiO_2$, can be extracted.

Thus, according to a first aspect of the invention, there is provided a method for determining relative composition by weight of ash material elements included in a paper product, the method comprising:

providing an X-ray source having a known X-ray spectra at each of a plurality of applied energies and an X-ray detector, the X-ray source and X-ray detector spaced apart for receiving the paper product;

sweeping a voltage power supply for powering the X-ray source at a plurality of applied energies, and at each applied energy: obtaining an X-ray response measurement from the X-ray detector with the paper product between the X-ray source and the X-ray detector and, obtaining an X-ray response measurement from the X-ray detector without the paper product between the X-ray source and the X-ray detector, generating an actual sensor response based on both obtained X-ray response measurements at each applied energy;

predicting a sensor response based on the known X-ray response spectra and known absorption coefficient values for each component of the paper product at each of the plurality of applied energies; and, comparing the actual sensor response and the predicted sensor response to compute ash component weights, and extracting relative weights of ash material elements based on the comparison.

According to a second aspect of the invention, there is provided an apparatus for measuring relative composition by weight of ash material elements included in a paper product, the apparatus comprising:

an X-ray source having a known X-ray spectra at each of a plurality of applied energies, and an X-ray detector, the X-ray source and X-ray detector spaced apart for receiving the paper product;

a voltage power supply that powers the X-ray source at a plurality of applied energies, the X-ray detector providing a plurality of X-ray response measurements at each of the plurality of applied energies, wherein a plurality of X-ray response measurements are obtained from the X-ray detector with the paper product between the X-ray source and the X-ray detector and, a plurality of X-ray response measurements are obtained from the X-ray detector without the paper product between the X-ray source and the X-ray detector, wherein an actual sensor response is obtained based on both the plurality of measurements;

a means for predicting a sensor response based on the known X-ray response spectra and known absorption coefficient values for each component of the paper product at each of the plurality of applied energies; and, a means for computing ash component weights by comparing the actual sensor response and the predicted sensor response, and extracting relative weights of ash material elements based on the comparison.

Advantageously, the system and method of the invention avoids being a 'measure-and-calibrate' approach, but rather, an approach that requires a derivation of the composition from known physical constants. This approach includes: 1. the use of a well-characterized X-ray tube (spectrum calculated and adjusted); 2. the use of fundamental absorption coefficients of the elements to be measured available as known in the public domain; 3. a measurement of ash through the numerical (theoretical) prediction of the sensor response; 4. the use of a fast scanning high voltage power supply to change the x-ray spectra; and, 5. a unique filter to improve the separation between the different types of ashes.

BRIEF DESCRIPTION OF THE DRAWINGS

These and other objects, features and advantages of the present invention will become apparent from the following detailed description of illustrative embodiments thereof, which is to be read in connection with the accompanying drawings, in which.

DETAILED DESCRIPTION OF THE INVENTION

The present invention is directed to an apparatus and method for measuring the relative material composition of ash content in a paper (web or sheet) product. Particularly, a novel technique implementing an X-ray gauge (sensor) is devised for measuring the relative material composition of ash content in flat sheet paper material. According to one embodiment, a careful characterization of the x-ray gauge is provided whereby the sensor being used calculates ash content from fundamental physical parameters.

Figure 1:
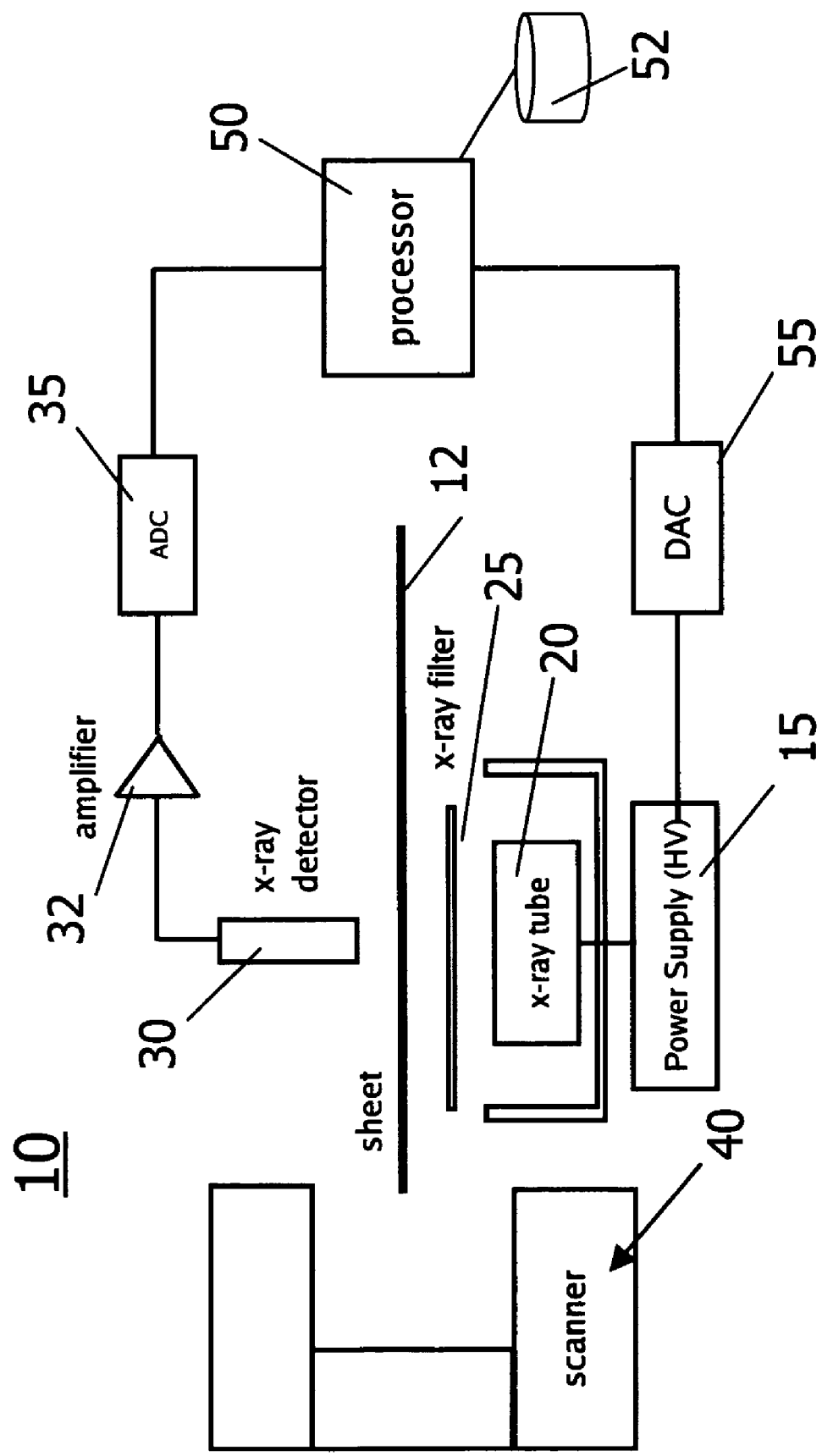
FIG. 1 illustrates a system 10 for determining relative ash content in a (web) paper sheet according to the invention.

FIG. 1 illustrates a system 10 for determining relative ash content in a (web) paper sheet according to the invention. The system 10 includes an x-ray absorption measurement system with X-rays generated using an X-ray tube 20. The system may include a scanner device 40 operable for moving the sensor and receiver across the web. A variable high voltage power supply 15 is used to generate x-rays over a wide range of energies. In this manner, according to the invention, a measurement of absorption of x-rays is conducted over such a range of energies to determine ash composition information. In one embodiment, the single x-ray source operated using a variable high voltage supply powers the X-ray tube 20 between 4.0 KV and 6 KV, for example.

According to the invention, X-ray tube 20, operating under control of programmable control device (processor) 50 provides signals that control the high-voltage power supply 15 used in the generation of the X-rays at the variable energies. Particularly, processor 50 provides digital signals that are converted by Digital-to-Analog converter 55 to control the high-voltage power supply and provide sweep signals used to produce X-ray signals across a broad energy spectra. That is, the programmable control device 50 operatively controls the high voltage supply to sweep the voltage (energies). The high voltage is 'swept', halting at every 100 or 200 V, for example, although it is understood that these programmed voltage increments may be varied. The x-rays are then passed through the paper sample (sheet) 12 whose ash content is to be measured. At each voltage level, an x-ray detector device 30 makes a measurement for a predetermined amount of time. In one embodiment, the measurement is made for up to about 50 ms, but this measurement time is configurable. The detector 30 includes an X-ray sensor or like total energy receiver device such as an ion chamber. Other detectors are possible including solid-state devices. An amplifier 32 is provided to enhance the small signal from the ion chamber and in the end the receiver produces a voltage proportional to the received x-ray energy per unit time. In a manner as will be described herein, the detector response is recorded at every voltage setting. Signals representing these detected values are converted by Analog-to-Digital converter device 35 input and processing by processor 50 and for recordation in a memory storage device 52.

As further shown in FIG. 1, in an effort to enhance the composition analysis, an X-ray filter device 25 may be provided that filters the x-rays and reduces a 'washing out' effect of the absorption spectra edges when a total signal measured in the detector is the summed multiplication of the energy x the absorption probability. In one example embodiment, the X-ray filter is a 70 g/cm$^2$ thick aluminum plate, however one skilled in the art will recognize that a filters of other thicknesses may be implemented depending upon the product elements being analyzed. Preferably, a unique X-ray filter is implemented to improve the separation between the different types of ashes.

Figure 2:
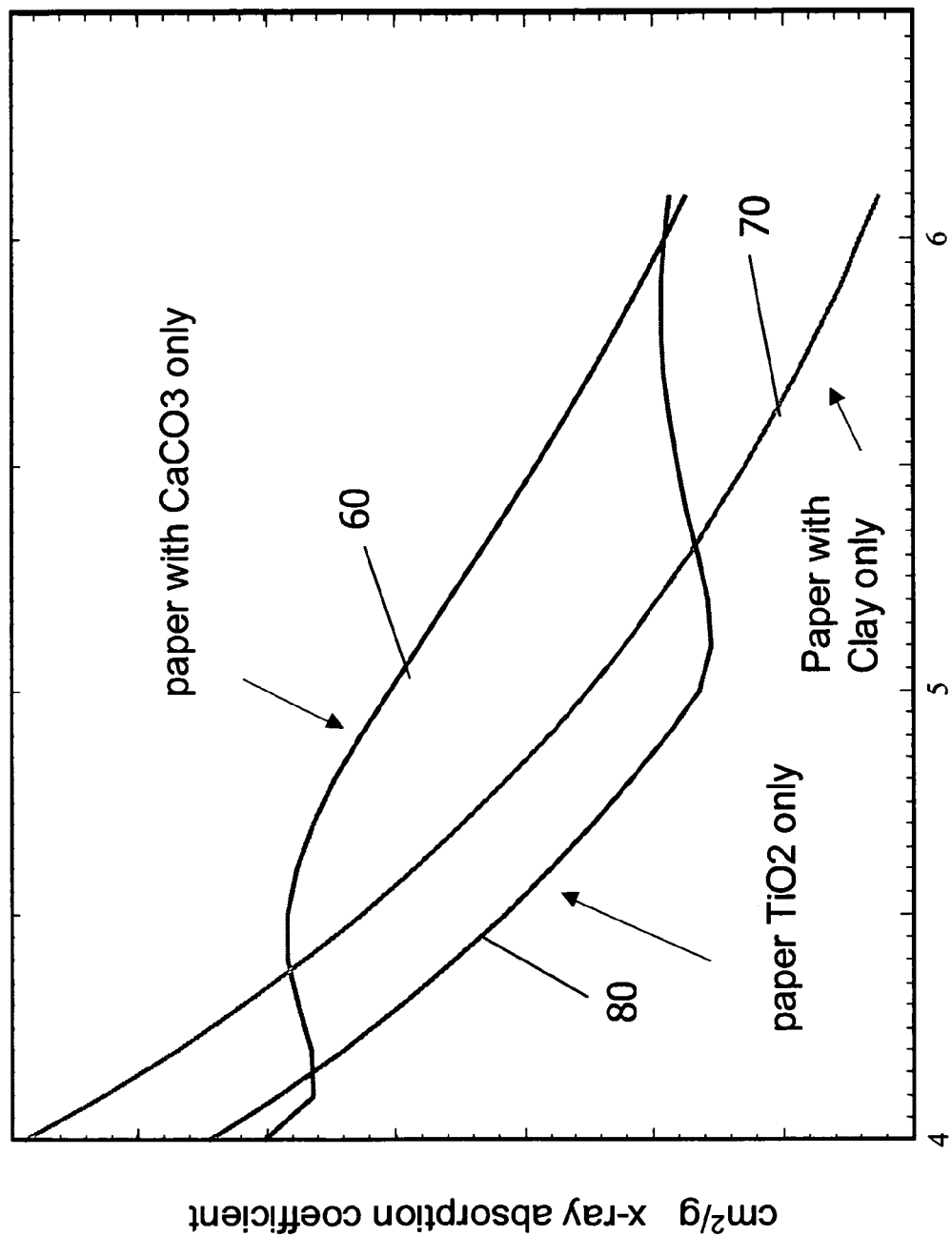
FIG. 2 depicts the absorption curves that are calculated according to the present invention to be compared with real data according to the invention; and, FIGS. 3A and 3B depict a method 100 used in the calculation of the weight basis for each of the constituent materials in the paper ash according to the invention.

FIG. 2 depicts the absorption curves that are calculated according to the present invention by processor 50, and which are compared to real data as will be explained in greater detail hereinbelow. The examples shown are for three (3) paper (sheet) samples with only one of each of the ash components of interest—CaCaO$_3$, Clay, and TiO$_2$. As shown in FIG. 2, the absorption coefficients are plotted against the applied X-ray tube voltage (X-ray energies). In the sensor response curves depicted in FIG. 2, the above-mentioned sharp edges are "washed out" because of the fact that the x-ray tube produces a wide range of energies. Thus, as shown in FIG. 2, most elements have very characteristic x-ray absorption spectra, i.e., the number of x-ray that can pass through the material changes drastically with the energy of the x-rays. Materials in ash content, e.g., additives such as CaCaO$_3$, Clay, and TiO$_2$, have distinct x-ray absorption spectrum labeled 60, 70, 80 respectively, in FIG. 2. In particular, two of the elements of interest to the paper making industry, Calcium and Titanium, have such absorption features depicted at about 4 and 5 KeV, the unit of energy normally used with X-rays. Clay, the other common ingredient has no absorption edges in the region 3-10 KeV and neither does cellulose—their x-ray absorption is a smooth decrease with increasing x-ray energy.

According to the technique of the invention, using tabulated absorption cross section, the known x-ray tube spectra and, the observer sensor response function (i.e., graph of the sensor signal versus the applied high voltage to the generating x-ray tube), a non-linear least square minimization technique may be used to extract the relative mounts of the ash constituents (e.g., CaCO$_3$, TiO$_2$ and Clay in the example embodiment described). In this technique, the total amount of ash and the paper Basis Weight are presumed known. In another embodiment of this invention, the moisture content and BW are known and the absolute amounts of ash constituent materials, e.g., CaCO3, TiO2 and Clay, may be calculated. In another embodiment, one of the ash components may be absent entirely and the amount of the remaining two elements calculated.

Figure 3A:
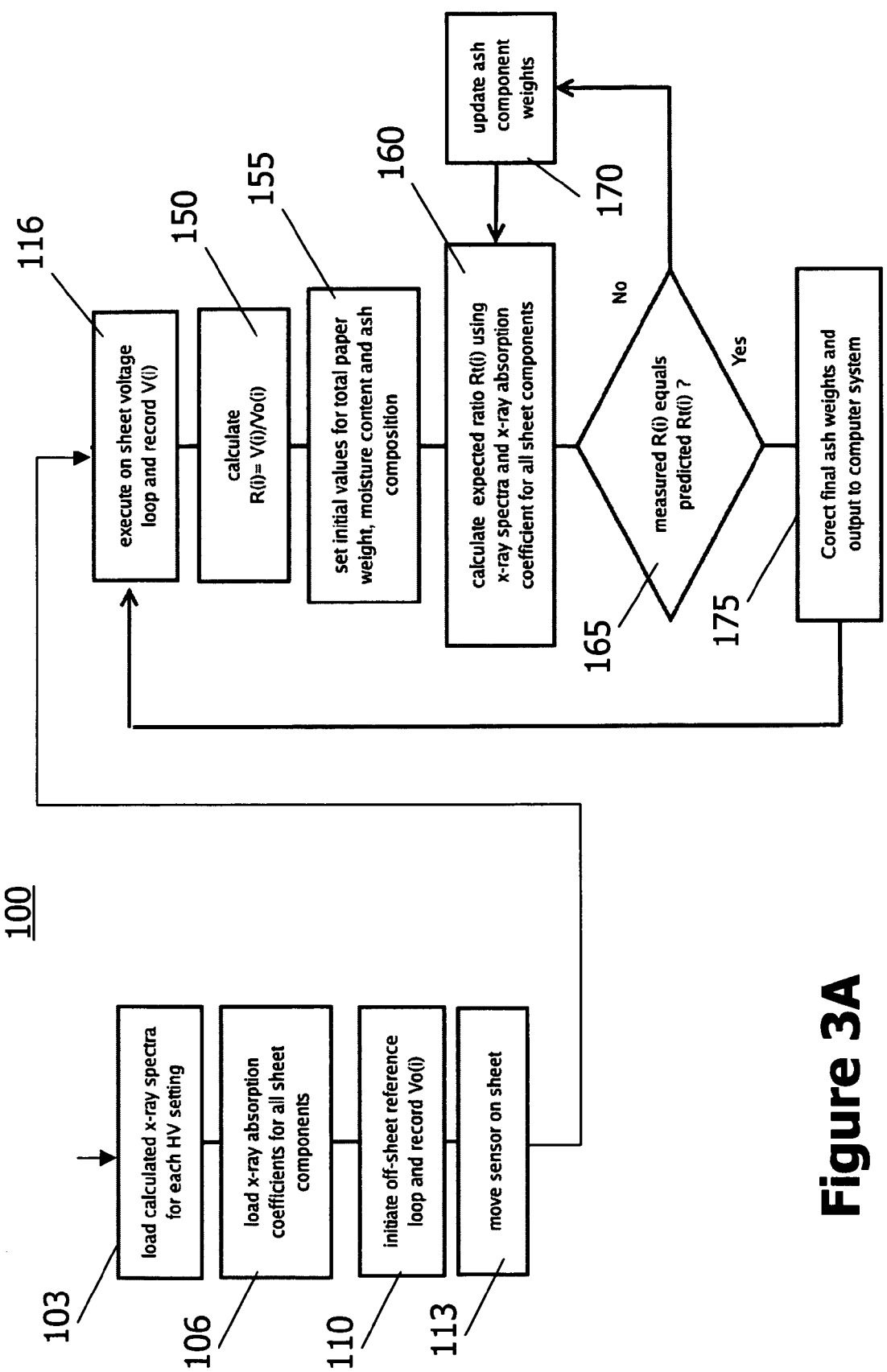
Figure 3B:
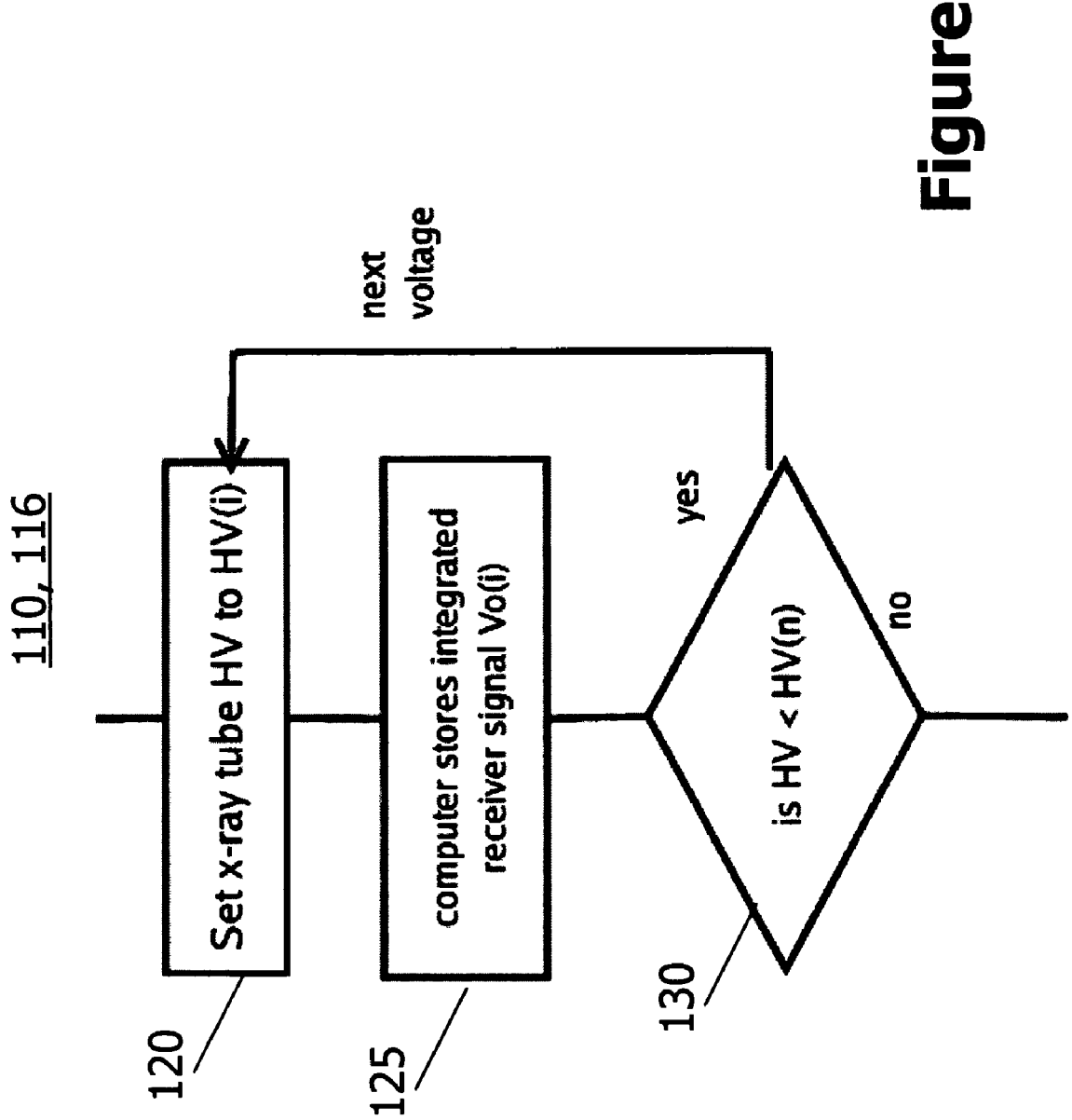

FIGS. 3A and 3B depict the method 100 used in the calculation of the weight basis for each of the constituent materials in the ash. According to the method 100, a sensor response signal is calculated that comprises a ratio of the X-ray detector (sensor) signal without the sheet (web) in place between the X-ray tube and the X-ray detector, and then with the sheet (web) in place between the X-ray tube and the X-ray detector. As shown in FIG. 3A, there is depicted the first step 103 of loading calculated X-ray spectra for each applied high voltage (HV) setting. This step 103 corresponds to obtaining the above-mentioned known X-ray tube spectra. Then, as depicted at a next step 106, the X-ray absorption coefficients for all sheet components (including ash constituent materials) are loaded and stored in a memory storage device for later reference. Then, as depicted at step 110, in an off-line process without the sheet (web) in place in the scanner, the X-ray tube voltage is set to an initial value (HV) and the X-ray sensor output $V_o(0)$ is obtained and recorded. Then, as will be described in greater detail hereinbelow with respect to FIG. 3B, a measurement reference loop is entered (without the sheet (web) in place) whereby the applied X-ray tube voltage is incremented over a desired range of values HV(i) where i=0, ... , n, and the sensor detector output is measured $V_o(i)$ over the entire range of incremented values HV(i). In one embodiment, high voltage power supply values are applied to the X-ray tube sensor over a range, e.g., 3.8 to 6.2 keV at a voltage increment value anywhere between 50 V-200 V, for example. The measured X-ray detector values for the entire range of incremented values HV(i) are recorded without the sheet in place.

Then, referring to FIG. 3A, step 113, there is depicted the further step of loading the sheet (web) in the sensor structure of FIG. 1 and, at step 116, performing the measurement loop as depicted in FIG. 3B, to obtain a sensor detector output V(i) over the range of incremented values HV(i), where i= 0, ... , n. Particularly, execution of step 116 is depicted in FIG. 3B as comprising the measurement loop including a first step 120 representing the step of setting the X-ray tube voltage to an initial value (HV) and then incrementing the value HV(i) by a predetermined amount over the desired range. As mentioned, the incremented high voltage power supply values are programmed to be evenly spaced apart, e.g., at a voltage increment anywhere between 50 V-200 V, however, this is configurable. Then, at step 125, the integrated receiver output signal V(i) is obtained (amplified, processed and converted to values for use by a computer) and the computer stores the integrated receiver output signal V(i) value for that applied sensor input voltage. Then, as depicted at step 130, a determination is made as to whether the last applied high voltage power supply voltage increment, HV(n), has been reached. Not until the last measurement has been obtained at HV(n), will the measurement loop return to step 120 where the next power supply increment HV(i) is applied.

As mentioned, the measurement loop is carried out at reference (off-sheet as depicted at step 110, FIG. 3A) as well as during measurement (on-sheet as depicted at step 110, FIG. 3A) and the ratio of the detector (output sensor) signal with and without the sheet is the sensor response. Thus, according to the method 100, for each applied HV(i) voltage, the sensor output values $V_o(i)$ are recorded by the processor device for each applied voltage to the tube. The example measurement sequence described thus includes a background run in which the sheet is removed from the sensor. The high voltage scan is carried out, for example, in a range from 3.8 KV to 6.2 KV (=HV(n) for example) in steps of 100 V, for example. All data points (voltages) are recorded by processor device 50 (FIG. 1). The same measurement is carried out with the sheet between X-ray tube and detector as depicted at step 116, FIG. 3A. In one embodiment, a fast scanning high voltage power supply is used to change the x-ray spectra such that the system may perform the measurement loop rapidly (e.g., is scanned at 1.0 sec. for 20 voltage data points).

Returning to step 150, FIG. 3A, the computer or processor device then calculates the ratios that comprise the sensor response function. This is represented at step 150 as comprising the steps of calculating $R(i)=V(i)/V_o(i)$ for each applied voltage value with and without the sheet in place. Then, as indicated at step 155, the initial values for the total paper weight, moisture content and ash composition (elements) are set as these are known beforehand.

The characterization of the x-ray tube spectrum is an essential ingredient in this technique. Thus, as shown in FIG. 3A, step 2A, a first guess (a theoretical or "expected") sensor response ratio $R_t(i)$ is calculated using the calculated X-ray spectra (obtained at step 103) and the X-ray absorption coefficients for all sheet components (obtained at step 106). Quantitatively, the first guess or expected response value is $$R_t = \frac{V^t}{V_o^t},$$

where $$V_o^t = \int_0^{E\max} I(E) \cdot E \cdot e^{\left(-\sum_{j=1}^{n} \mu_j m_j\right)} dE \text{ and,}$$

$$V^t = \int_0^{E\max} I(E) \cdot E \cdot e^{\left(-\sum_{j=1}^{n} \mu_j m_j - \sum_{j=k}^{3} \mu_k w_k\right)} dE.$$

In these equations, I(E) is the relative X-ray tube spectral intensity and "E" is the energy of the x-ray. Particularly, the sum in the first equation is over all those materials present between the source and receiver when not measuring the sheet (these include air and the receiver window), $\mu_j$ is the absorption coefficient of the material and $m_j$ is the mass thereof, $\mu_k$ is the absorption coefficient of the paper components (including the moisture and cellulose as well as the ash) and wk is the mass thereof, and Emax is the maximum energy output by the x-ray tube at the applied high voltage.

Then, at step 165, a determination is made as to whether the measured R(i) is equal to the first guess or predicted response ratio $R_t(i)$. If at step 165 it is determined that the measured R(i) is not equal to the first guess or predicted response ratio $R_t(i)$, then the process proceeds to step 170 where the ash component weights are updated, e.g., using an applied 'non-linear chi-squared minimization' technique, and the expected ratio $R_t(i)$ at the new ash weight values, are calculated. That is, as would be known to skilled artisans, the ash weights are varied to match the measurement to the theoretical sensor ratios. This sequence of steps 160, 165 and 170 is repeated until the observed sensor ratio matches the model calculation. At that point the ash component weight values are corrected slightly and presented to the user, as indicated at step 175. A final correction may be optionally made to the sensor result values by calibrating against an independent, laboratory-type chemical analysis. That is, in addition to analyzing paper samples in accordance with the present invention, a chemical analysis technique may be optionally performed. A comparison of these two provides a small correction to be added to/substracted from the sensor results as acquired above.

Thus, the characterization of the x-ray tube spectrum is an essential ingredient in this technique. A first guess spectrum is calculated based on atomic formula; but corrections may be made by taking lab measurements on pure elements of known thickness. This is because X-ray absorption cross sections are quite well known. The better the x-ray tube spectrum is known, the more accurate the results. Utilizing these results and knowing the total basis weight and a first guess at the fractions of each ash component, the programmed processor or like computer device calculates the expected sensor ratio (sensor response function) at each voltage setting. The publically available absorption data are used for water, cellulose, $CaCO_3$, Clay and $TiO_2$. After comparing this to the measured data, the computer program corrects the relative amount of $CaCO_3$, $TiO_2$ and Clay until the theoretically predicted sensor response function matches that measured response function. The last step is carried out using non-linear least square minimization, or like minimization technique.

Thus, according to the invention, by varying the X-ray gauge rapidly, measuring the absorption at each energy level and comparing this to data stored in a memory device associated with the computer device (including tables of fundamental physical parameters for all known elements) available from the U.S. National Institute of Standards (NIST) or the Sandia National Laboratories), the relative fractions of materials in ash content, e.g., $CaCO_3$, $TiO_2$ and Clay are extracted.

It is understood that the relative weights of other constituent materials found in web or paper products are determinable according to the teachings of the present invention. Generally, the present invention may be used for any application where the constituents of a product are known in type and the constituents have distinct X-ray absorption spectra. Thus, for instance, the invention may be used for determining relative weights of elements in alloy coatings.

While the invention has been particularly shown and described with respect to illustrative and preformed embodiments thereof, it will be understood by those skilled in the art that the foregoing and other changes in form and details may be made therein without departing from the spirit and scope of the invention which should be limited only by the scope of the appended claims.

What is claimed is:

1. An apparatus for measuring relative composition by weight of ash material elements included in a paper product, the apparatus comprising:
    an X-ray source having a known X-ray spectra at each of a plurality of applied energies and an X-ray detector, said X-ray source and X-ray detector spaced apart for receiving said paper product;
    a voltage power supply that powers the X-ray source at a plurality of applied energies, said X-ray detector providing a plurality of X-ray response measurements at each of said plurality of applied energies, wherein a plurality of X-ray response measurements are obtained from the X-ray detector with said paper product between said X-ray source and said X-ray detector and, a plurality of X-ray response measurements are obtained from the X-ray detector without said paper product between said X-ray source and said X-ray detector, wherein an actual sensor response is obtained based on both said plurality of measurements;
    a means for predicting a sensor response based on said known X-ray response spectra and known absorption coefficient values for each component of said paper product at each of said plurality of applied energies; and,
    a means for computing ash component weights by comparing said actual sensor response and said predicted sensor response, and extracting relative weights of ash material elements based on said comparison.

2. The apparatus as claimed in claim 1, wherein said actual sensor response is a first ratio $R(i)=V(i)/V_o(i)$, where $V(i)$ is an absorption response measurement obtained with said paper product between said X-ray source and said X-ray detector and $Vo(i)$ is an absorption response measurement obtained without said paper product between said X-ray source and said X-ray detector for each applied energy increment (i).

3. The apparatus as claimed in claim 2, wherein said predicted sensor response comprises a second ratio $R_f(i)$ obtained by applying said known absorption coefficient values for each component of said paper product to the known X-ray response spectra at each of a plurality of applied energies.

4. The apparatus as claimed in claim 3, further comprising means for storing said X-ray response spectra for each applied voltage setting, and, storing said one or more absorption coefficient values for each component of said paper product.

5. The apparatus as claimed in claim 3, wherein said ash material elements included in a paper product include $CaCO_3$, $TiO_2$ and Clay.

6. The apparatus as claimed in claim 4, wherein said storing means stores initial values for a total paperweight and component weights for said ash composition.

7. The apparatus as claimed in claim 6, further comprising control means for computing ash component weights according to a comparison of said first and second ratios, said stored total paper weight and said ash component weight values.

8. The apparatus as claimed in claim 1, further comprising control means for sweeping said voltage power supply for powering the X-ray source at a plurality of applied energies.

9. The apparatus as claimed in claim 8, wherein said control means sweeps said voltage power supply for powering the X-ray source at voltage increments between 1 KeV and 10 KeV.

10. The apparatus as claimed in claim 9, wherein said voltage increment is a value ranging between 50 V to 200 V.

11. The apparatus as claimed in claim 1, further comprising an X-ray filter means provided between said X-ray source and said paper product for improving separation between different types of ash materials.

12. A method for determining relative composition by weight of ash material elements included in a paper product, the method comprising:
    providing an X-ray source having a known X-ray spectra at each of a plurality of applied energies and an X-ray detector, said X-ray source and X-ray detector spaced apart for receiving said paper product;
    sweeping a voltage power supply for powering the X-ray source at a plurality of applied energies, and at each applied energy: obtaining an X-ray response measurement from the X-ray detector with said paper product between said X-ray source and said X-ray detector and, obtaining an X-ray response measurement from the X-ray detector without said paper product between said X-ray source and said X-ray detector, generating an actual sensor response based on both obtained X-ray response measurements at each applied energy;

predicting a sensor response based on said known X-ray response spectra and known absorption coefficient values for each component of said paper product at each of said plurality of applied energies; and, comparing said actual sensor response and said predicted sensor response to compute ash component weights, and extracting relative weights of ash material elements based on said comparison.

13. The method as claimed in claim 12, wherein said generating an actual sensor response comprises calculating a first ratio $R(i)=V(i)/V_o(i)$, where $V(i)$ is an absorption response measurement obtained with said paper product between said X-ray source and said X-ray detector at an applied energy increment "i" and, $V_o(i)$ is an absorption response measurement obtained without said paper product between said X-ray source and said X-ray detector at each applied energy increment i.

14. The method as claimed in claim 13, wherein said predicting a sensor response comprises: calculating a second ratio $R_r(i)$ obtained by applying said known absorption coefficient values for each component of said paper product to the known X-ray response spectra at each of a plurality of applied energies.

15. The method as claimed in claim 13, implemented to determine relative composition by weight of $CaCO_3$, $TiO_2$ and Clay material elements included in a paper product.

16. The method as claimed in claim 14, further comprising: storing said X-ray response spectra for each applied voltage setting, and, storing said one or more absorption coefficient values for each component of said paper product.

17. The method as claimed in claim 16, further comprising: storing initial values for a total paperweight and component weights for said ash composition.

18. The method as claimed in claim 17, further comprising: computing ash component weights according to a comparison of said first and second ratios, said stored total paper weight and said ash component weight values.

19. The method as claimed in claim 18, wherein said step of computing ash component weights comprises: utilizing a non-linear least square minimization technique to correct the relative amount of ash component material until the predicted sensor response matches the actual sensor response.

20. A computer program product comprising computer usable medium having computer usable program code for determining relative composition by weight of ash material elements included in a paper product utilizing an X-ray source having a known X-ray spectra at each of a plurality of applied energies and an X-ray detector, the computer program product including:

computer usable program code for sweeping a voltage power supply for powering the X-ray source at a plurality of applied energies, and at each applied energy: obtaining an X-ray response measurement from the X-ray detector with said paper product between said X-ray source and said X-ray detector and, obtaining an X-ray response measurement from the X-ray detector without said paper product between said X-ray source and said X-ray detector, computer usable program code for generating an actual sensor response based on both obtained X-ray response measurements at each applied energy;

computer usable program code for predicting a sensor response based on said known X-ray response spectra and known absorption coefficient values for each component of said paper product at each of said plurality of applied energies; and, computer usable program code for comparing said actual sensor response and said predicted sensor response to compute ash component weights, and extracting relative weights of ash material elements based on said comparison.

* * * * *